United States Patent [19]

Larijani

[11] Patent Number: 5,756,514
[45] Date of Patent: May 26, 1998

[54] METHODS FOR TREATMENT AND PREVENTION OF DRUG-INDUCED PRURITUS WITH SEROTONIN TYPE 3 RECEPTOR ANTAGONISTS

[76] Inventor: Ghassem E. Larijani, 205 Sproul Rd., Villanova, Pa. 19085

[21] Appl. No.: 775,455

[22] Filed: Dec. 30, 1996

[51] Int. Cl.⁶ .................................................. A61K 31/44
[52] U.S. Cl. ........................ 514/299; 514/305; 514/397
[58] Field of Search ................................. 514/299, 305, 514/397

[56] References Cited

PUBLICATIONS

Crighton et al, Anaesthesia, 51(2), pp. 199–200, Feb. 1996.
Biosis AN 94:536734 Heim et al, Anaesthesist, 43(8), pp. 504–509, 1994.
Schworer et al, Clin. Investig, 71:659–662, 1993.
Naylor et al, Eur J Anaesthesiology, 9(Sup 6):3–10, 1992.
Gyermek, J Clin Pharmacol, 35:845–855, 1995.
Oxford et al, Progress in Medicinal Chem, vol. 29:239–270, 1992.
Schworer, H. and Ramadori, "Improvement of cholestatic pruritus by ondansetron", *Lancet* 1993 341:1277.
Schworer et al., "Relief of cholestatic pruritus by a novel class of drugs: 5–hydroxytryptamine type 3 (5–HT$_3$) receptor antagonists: effectiveness of ondansetron", *Pain* 1995 61(1):33–37.

*Primary Examiner*—Rebecca Cook
*Attorney, Agent, or Firm*—Law Offices of Jane Massey Licata

[57] ABSTRACT

Methods of treating and preventing drug-induced pruritus in patients by administration of a serotonin type 3 antagonist are provided.

4 Claims, No Drawings

METHODS FOR TREATMENT AND PREVENTION OF DRUG-INDUCED PRURITUS WITH SEROTONIN TYPE 3 RECEPTOR ANTAGONISTS

This application claims the benefit of U.S. Provisional Application No. 60/024,646, filed Aug. 22, 1996.

BACKGROUND OF THE INVENTION

Epidural or intrathecal administration of opioids can provide excellent analgesia and is used increasingly in perioperative pain management. However, opioid-induced pruritus is a major problem associated with neuroaxial administration. The itching typically develops 2–5 hours after opioid administration and usually subsides after cessation of the treatment. Pruritis is also observed in patients following administration of other drugs such as antibiotics. Very little is known about this drug-induced pruritis and its treatment is often unsatisfactory.

Pruritus is also common in patients with cholestatic disease and chronic renal insufficiency. Conventional antipruritic therapy of cholestatic pruritus includes antihistamines and cholestyramine. Ondansetron has also been shown to relieve the symptoms of cholestatic pruritus for limited time periods. Schworer, H. and Ramadori, *Lancet* 1993 341:1277. In this case report, a 49-year-old woman with severe cholestatic pruritic was administered ondansetron 8 mg as a single intravenous injection. Itching was relieved within 30 minutes after the end of the injection and the effect lasted for 4 hours. Approximately 6 hours after the injection, she scored her pruritus as 3–4 on a scale of 1–10, with 10 being the most severe. A subsequent study was performed in 10 additional patients with cholestatic itch. Schworer et al., *Pain* 1995 61(1) :33–37. Ondansetron reduced or abolished pruritus within 30 to 60 minutes after injection. A 50% reduction of intensity of itch was observed for up to 6 hours after injection of 8 mg. It was concluded that serotonin may be involved in the generation and/or sensation of itching in cholestasis, and that relief of pruritus by ondansetron results from 5-HT3 receptor antagonism. It is suggested that 5-HT3 receptor antagonists may become a novel therapeutic tool in the treatment of cholestatic pruritus.

Unlike cholestatic pruritus, drug-induced pruritus can not be treated with conventional antipruritic therapies. Antihistamines are almost always ineffective in providing relief from the itching. Naloxone, a narcotic antagonist has proven effective in some patients with opioid-induced pruritis; however, administration of this drug oftentimes results in breakthrough pain as well as significant sympathetic stimulation. Accordingly, better treatments are need for this common side effect.

SUMMARY OF THE INVENTION

An object of the present invention is to provide a method of treating drug-induced pruritus in a patient comprising administering to a patient suffering from drug-induced pruritus a serotonin type 3 receptor antagonist.

Another object of the present invention is to provide a method for preventing drug-induced pruritus comprising administering to a patient being treated with a drug known to cause pruritis a serotonin type 3 receptor antagonist.

DETAILED DESCRIPTION OF THE INVENTION

It has now been found that administration of serotonin type 3 receptor antagonists to patients receiving opioid treatment can be used in the treatment and prevention of opioid-induced pruritus. Administration of serotonin type 3 receptor antagonists has also been found to be effective in alleviating pruritis induced by other drugs such as antibiotics.

Serotonin type 3 receptor antagonists such as ondansetron, granisetron and dolasetron mesylate are used in the treatment of a variety of conditions, including the nausea and vomiting induced by cancer chemotherapy and radiotherapy (as described, for example, in European Patent Specification No. 226266A). Administration of ondansetron has also been shown to be effective in relieving some of the itching associated with cholestatic pruritis in patients for up to 6 hours.

However, studies in patients with drug-induced pruritus now demonstrate that administration of the serotonin type 3 receptor antagonist, ondansetron, is effective in eliminating all itching resulting from drug-induced pruritus. In 3 out of 4 patients in the study, a single intravenous dose of either 4 or 8 mg of ondansetron was effective in alleviating all itching resulting from the opioid-induced pruritus for the duration of the opioid treatment. Itching disappeared completely within a few minutes of administration of the serotonin type 3 receptor antagonist and did not reappear. In addition, a single dose of 4 mg of ondansetron to a patient, intravenously, resulted in complete disappearance of itching caused by the antibiotic vancomycin.

Examples of other serotonin type 3 receptor antagonists which can be used in this method include, but are not limited to, granisetron hydrochloride and dolasetron mesylate. Appropriate dosages, routes of administration and pharmaceutical vehicles for these compounds are well known in the art. In the present invention, these compounds can be administered alone or in combination. In addition, an antihistamine or narcotic antagonist can be administered in conjunction with the serotonin type 3 receptor antagonist. These compounds can be administered upon appearance of symptoms of drug-induced pruritus. Alternatively, such compounds can be administered prior to appearance of these symptoms in a patient being treated with a drug known to cause pruritis to prevent the occurrence of drug-induced pruritus.

The following nonlimiting examples are provided to further illustrate the present invention

EXAMPLES

Example 1

Ondansetron was administered to four patients to treat pruritus caused by opioid administration Patient No. 1

The first patient was a 64-year-old man with stage A adenocarcinoma of the prostate who had undergone pelvic node dissection and radical prostatectomy. There were no intraoperative complications related to the surgery or anesthesia. Anesthesia consisted of morphine sulfate, midazolam, propofol, nitrous oxide, oxygen, isoflurane, and pancuronium bromide. The patient received a 5-mg bolus dose of preservative-free morphine sulfate intraoperatively by epidural catheter. In the postanesthesia care unit an infusion of preservative-free morphine sulfate through the epidural catheter was started at 0.8 mg/hour for postoperative pain.

On the first postoperative day, with adequate analgesia, the patient developed generalized pruritus. He was given diphenhydramine 50 mg intravenously without relief. The pruritus was unresponsive to a second dose of intravenous diphenhydramine 50 mg 8 hours later. The patient was then given a single dose of ondansetron 4 mg intravenously, which resulted in disappearance of the itching within three minutes. The patient continued to receive epidural morphine for two more days and pruritus did not reappear.

Patient No. 2

The second patient was a 60-year-old man with prostate carcinoma who had undergone elective laparoscopic pelvic node dissection under general anesthesia. He received ampicillin 1 gram intravenously and gentamicin 100 mg intravenously immediately before going to the operating room. The patient received thiopental, midazolam, fentanyl, isoflurane, succinylcholine, pancuronium, morphine sulfate, and droperidol for intraoperative anesthesia. He also received a loading dose of preservative free morphine sulfate 4 mg by epidural catheter intraoperatively. The anesthesia and surgery were uneventful. The epidural catheter was inadvertently removed in the recovery room.

Approximately 6 hours after the operation the patient complained of itching on his back and arms. The itching was severe, diffuse and bilateral, located anteriorly and posteriorly on the trunk. Diphenhydramine 50 mg orally was administered, but approximately 12 hours after the operation, the patient was still complaining of severe pruritus. At this time, he received a single intravenous dose of ondansetron 4 mg. The itching disappeared within a few minutes and did not reappear during the patient's hospital stay.

Patient No. 3

The third patient was a 56 year-old man testing positive for the HIV antibody who was seen in the emergency room for diffuse abdominal pain of 5 days duration. He was admitted. Computerized tomographic scan showed a distended and enlarged gall bladder. On admission, the patient was taking Bactrim DS, ranitidine, Maalox and Mycelex. He underwent laparoscopic cholecystectomy, cholangiogram and liver biopsy. Anesthesia consisted of midazolam, fentanyl, propofol, nitrous oxide, oxygen, isoflurane, rocuronium, neostigmine, and glycopyrrolate. The patient also received cefazolin sodium 1 gram in the operating room.

Shortly after arriving in the recovery room the man complained of severe pruritus of the abdomen and extremities. He was given diphenhydramine 50 mg intravenously without relief. Approximately 30 minutes after administration of the diphenhydramine the patient was still scratching his abdomen without any visible skin color changes. He was then given a single intravenous dose of ondansetron 8 mg, which resulted in complete relief of itching within 5 minutes. The itching did not reappear.

Patient No. 4

The fourth patient was a 35 year old women with squamous cell carcinoma of the cervix who underwent radical hysterectomy and left pelvic node dissection. General anesthesia consisted of midazolam, fentanyl, propofol, nitrous oxide, oxygen, isoflurane, and vecuronium. Immediately before induction of anesthesia, she was given a 5 mg loading dose of preservative-free morphine sulfate by epidural catheter, followed by an infusion of 0.4 mg/hour.

On the first post-operative day preservative-free morphine sulfate was infusing at a rate of 1 mg/hour with excellent analgesia. However, the woman complained of generalized pruritus, mostly on the back and abdomen, which started after she arrived in the recovery room. She was given ondansetron 4 mg intravenously, which resulted in some relief. A second dose of ondansetron 8 mg intravenously 15 minutes later did not provide more relief. Naloxone 40 micrograms intravenously was given and relieved the pruritus within five minutes, without the return of pain.

Example 2

Ondansetron was administered to a patient to treat pruritus caused by antibiotic administration A 27 year-old pregnant patient was admitted to the hospital for labor and delivery. The patient had a history of heart disease and was taking digoxin daily (0.25 mg orally). For delivery, the patient had an epidural catheter and received 15 ml of 3% chloroprocaine. The patient had a normal vaginal delivery. Post delivery, the patient received gentamicin (20 mg, intravenously) and vancomycin (1 gram, intravenously) for endocarditis prophylaxis. Approximately one hour after receiving the antibiotics, the patient developed a severe generalized itching. The patient was given a single dose of ondansetron (4 mg, intravenously) which resulted in complete disappearance of her itching within 5 minutes.

What is claimed is:

1. A method of treating drug-induced pruritus in a patient suffering from drug-induced pruritus comprising administering to the patient an effective amount of a serotonin type 3 antagonist.

2. The method of claim 1 wherein the serotonin type 3 antagonist is selected from a group consisting of ondansetron hydrochloride, granisetron hydrochloride and dolasetron mesylate.

3. A method of preventing drug-induced pruritus in a patient being treated with a drug known to cause pruritus comprising administering to the patient an effective amount of a serotonin type 3 antagonist.

4. The method of claim 3 wherein the serotonin type 3 antagonist is selected from a group consisting of ondansetron hydrochloride, granisetron hydrochloride and dolasetron mesylate.

* * * * *